US007988659B2

(12) United States Patent
Shibata et al.

(10) Patent No.: US 7,988,659 B2
(45) Date of Patent: Aug. 2, 2011

(54) INDWELLING BALLOON CATHETER FOR ENDOSCOPE

(75) Inventors: Hiroaki Shibata, Saitama (JP); Shinichi Matsuno, Kanagawa (JP)

(73) Assignee: Hoya Corporation, Tokyo (JP)

( * ) Notice: Subject to any disclaimer, the term of this patent is extended or adjusted under 35 U.S.C. 154(b) by 383 days.

(21) Appl. No.: 11/458,785

(22) Filed: Jul. 20, 2006

(65) Prior Publication Data

US 2007/0043324 A1    Feb. 22, 2007

(30) Foreign Application Priority Data

Jul. 20, 2005    (JP) ................................ P2005-209414

(51) Int. Cl.
    *A61M 3/00*     (2006.01)

(52) U.S. Cl. ......... 604/43; 604/98.01; 604/544; 604/32; 600/3

(58) Field of Classification Search .............. 604/43, 604/98.01, 282, 544, 32; 600/3
See application file for complete search history.

(56) References Cited

U.S. PATENT DOCUMENTS

| | | | | |
|---|---|---|---|---|
| 3,114,373 A * | 12/1963 | Andersen | ......... | 604/45 |
| 3,731,692 A * | 5/1973 | Goodyear | ......... | 128/207.15 |
| 4,300,550 A * | 11/1981 | Gandi et al. | ......... | 128/207.18 |
| 4,674,495 A * | 6/1987 | Orr | ......... | 128/207.14 |
| 4,771,777 A * | 9/1988 | Horzewski et al. | ......... | 606/194 |
| 4,983,166 A | 1/1991 | Yamawaki | | |
| 5,015,230 A * | 5/1991 | Martin et al. | ......... | 604/103.13 |
| 5,041,089 A * | 8/1991 | Mueller et al. | ......... | 604/103.09 |
| 5,087,247 A * | 2/1992 | Horn et al. | ......... | 604/98.01 |
| 5,098,412 A * | 3/1992 | Shiu | ......... | 604/523 |
| 5,292,305 A * | 3/1994 | Boudewijn et al. | ......... | 604/43 |
| 5,578,009 A * | 11/1996 | Kraus et al. | ......... | 604/95.04 |
| 5,649,909 A * | 7/1997 | Cornelius | ......... | 604/96.01 |
| 5,749,889 A * | 5/1998 | Bacich et al. | ......... | 606/198 |
| 5,807,311 A * | 9/1998 | Palestrant | ......... | 604/28 |
| 5,879,499 A * | 3/1999 | Corvi | ......... | 156/175 |
| 6,251,059 B1 * | 6/2001 | Apple et al. | ......... | 600/3 |
| 6,461,347 B1 * | 10/2002 | von Hoffmann | ......... | 604/508 |

(Continued)

FOREIGN PATENT DOCUMENTS

JP      62-167572      7/1987

(Continued)

OTHER PUBLICATIONS

English language Abstract of JP 9-099059.

(Continued)

*Primary Examiner* — Nicholas D Lucchesi
*Assistant Examiner* — Scott Medway
(74) *Attorney, Agent, or Firm* — Greenblum & Bernstein, P.L.C.

(57) ABSTRACT

An indwelling balloon catheter for an endoscope is provided with a flexible tube including a first lumen and a second lumen, the first lumen and the second lumen being arranged in parallel with each other and extending in an axial direction of the flexible tube over an entire length thereof, and a connector provided with a first connecting pipe and a second connecting pipe which protrude from a body of the connector, protruded portions of the first connecting pipe and the second connecting pipe being configured to be removably inserted into the first lumen and the second lumen, respectively. A cross sectional shape of the first lumen is a non-circular shape, a cross sectional shape of the first connecting pipe corresponding to the cross sectional shape of the first lumen. The first connecting pipe protrudes longer from the connector than the second connecting pipe.

13 Claims, 7 Drawing Sheets

U.S. PATENT DOCUMENTS 6,582,395 B1 6/2003 Burkett et al.
6,695,832 B2 * 2/2004 Schon et al. .................. 604/544

FOREIGN PATENT DOCUMENTS

| JP | 63-117768 | 5/1988 |
| --- | --- | --- |
| JP | 2-25256 | 2/1990 |
| JP | 3-074589 | 11/1991 |
| JP | 9-10219 | 1/1997 |
| JP | 9-099059 | 4/1997 |
| JP | 2001-299936 | 10/2001 |

OTHER PUBLICATIONS

English language Abstract of the corresponding Japanese Laid-Open Patent Publication No. HEI 1-171571 A (Jul. 6, 1989).

Japan Office action, dated Sep. 2010 along with an english translation thereof.

* cited by examiner

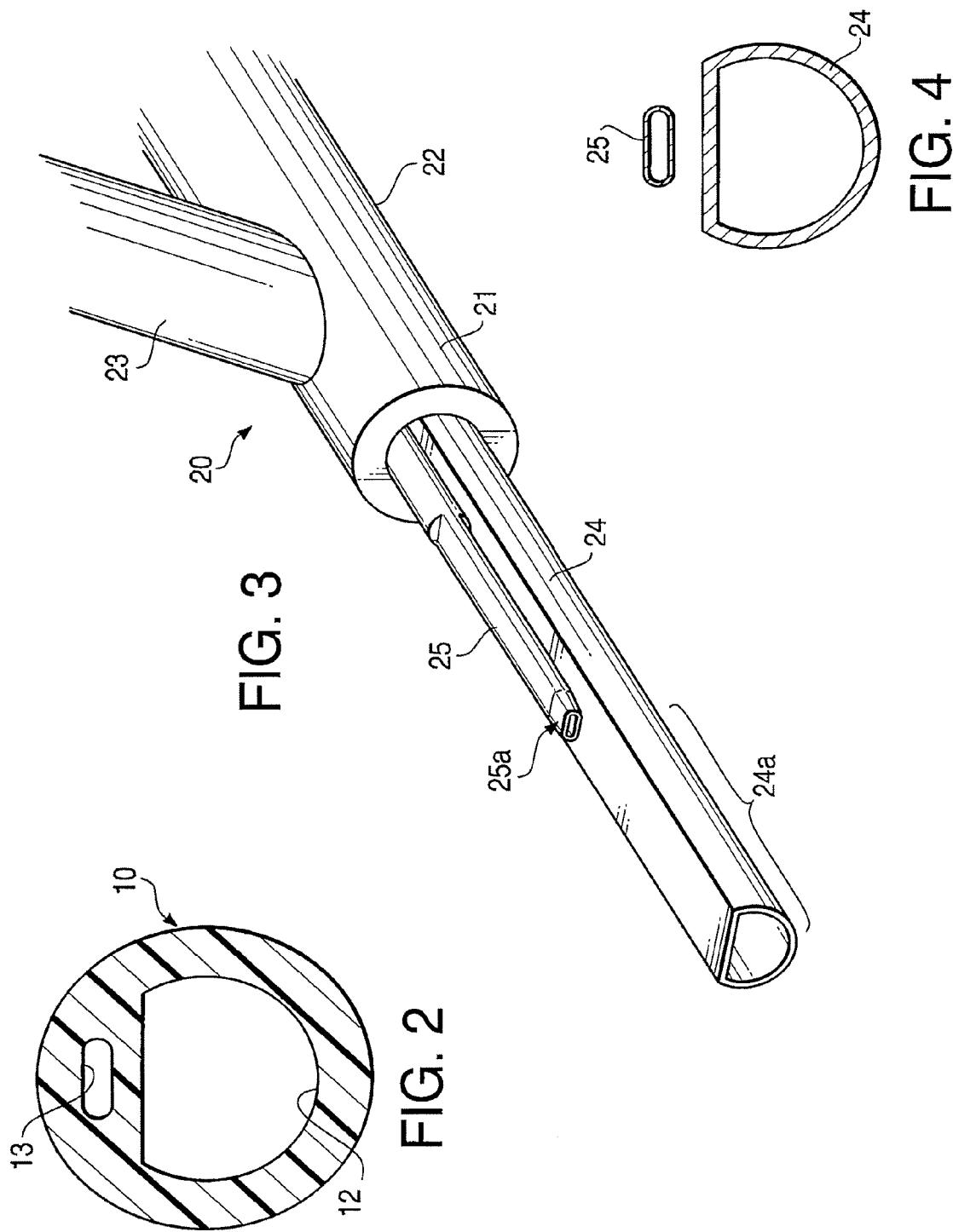

INDWELLING BALLOON CATHETER FOR ENDOSCOPE

BACKGROUND OF THE INVENTION

The present invention relates to an indwelling balloon catheter for an endoscope.

When the indwelling balloon catheter is used, a flexible tube, which is a catheter, is guided to an objective region in the body cavity, through a treatment tool channel of the endoscope. Then, only the endoscope is pulled out from the body cavity, thereby leaving the flexible tube thereat.

For this purpose, a connector, which cannot pass through the treatment tool channel of the endoscope, is detachably provided at the proximal end of the flexible tube, and after the endoscope is pulled out from the body cavity, the connector is connected to the proximal end of the flexible tube. An example of such a configuration is disclosed, for example, in Japanese Patent Provisional Publication No. HEI 09-99059.

If such an indwelling catheter is used for radiation therapy with a small radiation source, in which a small chip of radiation source is introduced inside the tip end of the catheter, and radiation therapy is performed from the inside of the body, a balloon catheter provided with an expansible/contractible balloon at the tip end is used. With such a configuration, the distal end of the indwelling catheter can be secured stably inside the body cavity. Examples of such a configuration is disclosed in Japanese Patent Publication No. HEI 3-74589 and Japanese Utility Model Provisional Publication HEI 02-25256.

The balloon catheter as described above requires a main lumen for a passage that is used for introducing a radiation source to the tip end, and a sub lumen for ventilation that is used to feed air to expand/contradict the balloon. The sub lumen may have a smaller cross-sectional area than the main lumen.

Since such a sub lumen for ventilation has a relatively small diameter of about 0.3-0.5 mm, there is a difficulty in inserting a sub lumen connecting pipe and a main lumen connecting pipe into the sub lumen and the main lumen, respectively, simultaneously, in an endoscopic treatment room generally having a relatively dark environment. It has occurred that a series of procedures was often interrupted in order to connect the proximal end of the catheter to the connector. Thus, the conventional balloon catheter may impose a burden to operators and a patient.

SUMMARY OF THE INVENTION

Aspects of the invention are advantageous in that an improved indwelling balloon catheter for an endoscope is provided. In the indwelling balloon catheter, insertion of the main lumen connecting pipe into the proximal end of the main lumen, and insertion of the sub lumen connecting pipe into the proximal end of the sub lumen can be performed relatively easily.

According to aspects of the invention, there is provided an indwelling balloon catheter for an endoscope, which is provided with a flexible tube including a first lumen and a second lumen, the first lumen and the second lumen being arranged in parallel with each other and extending in an axial direction of the flexible tube over an entire length thereof, and a connector provided with a first connecting pipe and a second connecting pipe which protruded from a body of the connector, protruded portions of the first connecting pipe and the second connecting pipe being configured to be removably inserted into the first lumen and the second lumen, respectively. A cross sectional shape of the first lumen is a non-circular shape, a cross sectional shape of the first connecting pipe corresponding to the cross sectional shape of the first lumen. The first connecting pipe protrudes longer from the connector than the second connecting pipe.

The flexible tube may be a double lumen flexible tube which is configured such that the first lumen and the second lumen are formed integrally over the entire length of the flexible tube.

The cross sectional shape of the second lumen may have a flat portion on the first lumen side, and wherein the cross sectional shape of the second connecting pipe has a flat portions corresponding to the flat portion of the second lumen.

The second connecting pipe may be tapered so that a portion closer to a tip end is smaller in size.

A cross sectional shape of the first lumen may be D-shaped with a flattened surface facing the second lumen, a cross sectional shape of the first connecting pipe corresponds to the cross sectional shape of the first lumen.

A portion of the first connecting pipe protruding farther from a tip end of the second lumen may be configured to be tapered to have a smaller size at a portion closer to the tip end of the first connecting pipe.

The second connecting pipe may be arranged obliquely with respect to the first connecting pipe such that a portion closer to the tip end of the second connecting pipe is spaced farther from the first connecting pipe, the second connecting pipe being elastically deformed to be parallel with the first connecting pipe.

The second connecting pipe may be slidable with respect to the first connecting pipe in an axial direction of the first connecting pipe.

The first lumen is a passage lumen allowing a predetermined substance to pass through, and the second lumen may be a ventilation lumen for feeding air therethrough.

The predetermined substance may include a small radiation source.

Each of the second lumen and the second connecting pipe may have a rounded-rectangular cross section.

BRIEF DESCRIPTION OF THE ACCOMPANYING DRAWINGS

FIG. 2 is a cross-sectional view of the indwelling balloon catheter taken along line II-II of FIG. 1, according to aspects of the first embodiment of the invention.

FIG. 3 is a partial perspective view of a connector according to aspects of the first embodiment of the invention.

FIG. 4 is a cross-sectional view of the indwelling balloon catheter taken along line IV-IV of FIG. 1.

DETAILED DESCRIPTION OF THE EMBODIMENTS

Figure 1:
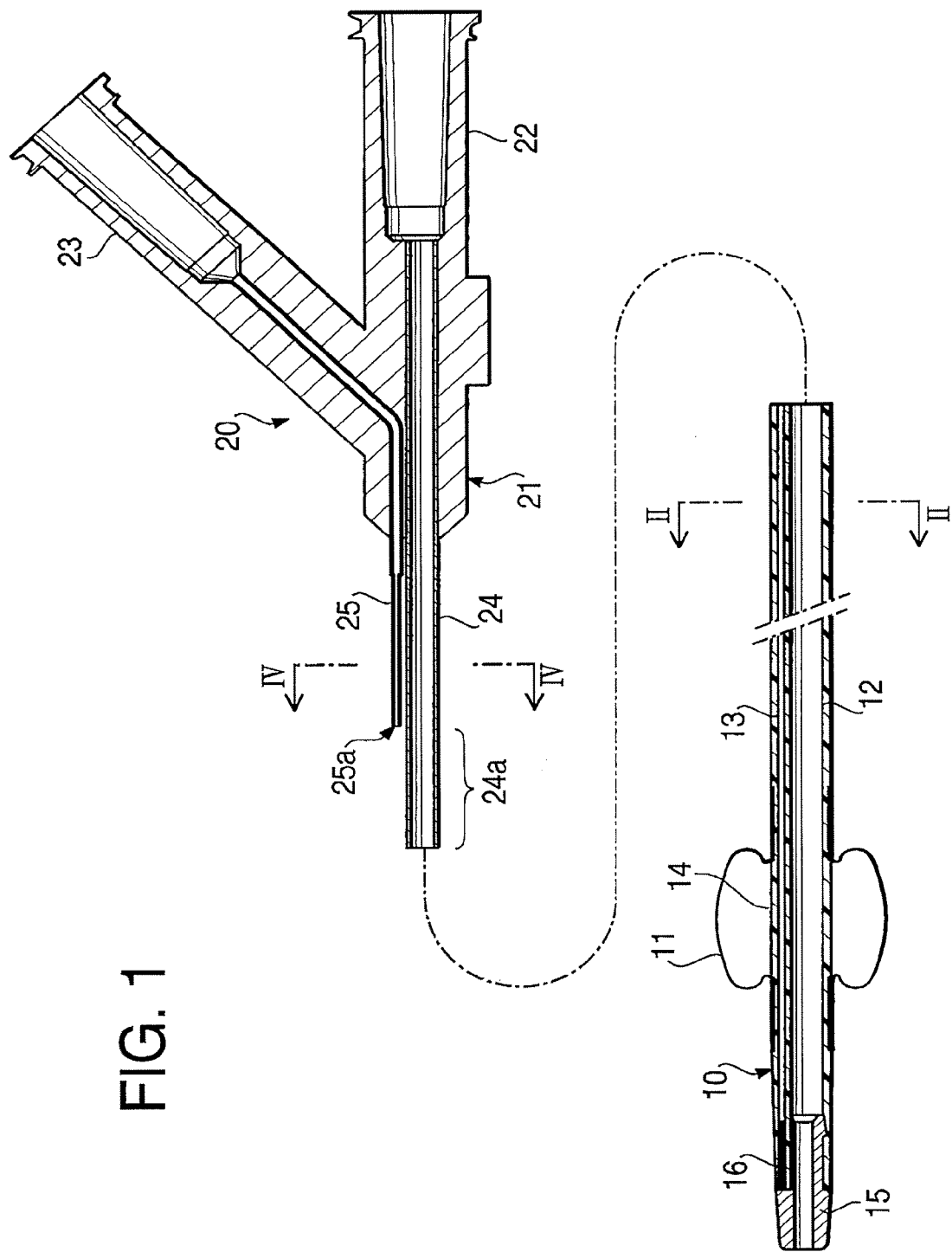
FIG. 1 is a cross-sectional side view showing general configuration of an indwelling balloon catheter for an endoscope according to a first embodiment of the invention.

FIG. 1 shows an indwelling balloon catheter for a endoscope according to aspects of a first illustrative embodiment of the invention. The indwelling balloon catheter is provided with a flexible tube 10 which can be inserted into a treatment tool channel (not shown) of an endoscope. On an outer peripheral surface of a distal end portion of the flexible tube 10, an expansible/contractible balloon 11 is secured.

As shown in FIG. 2, which is a cross section taken along line II-II of FIG. 1, the flexible tube 10 is configured as a double lumen tube including a main lumen 12 through which a minute radiation source is inserted, and a sub lumen 13 having a smaller cross sectional area than the main lumen 12, which are arranged in parallel with each other along an axial direction over an entire length of the flexible tube 10.

The main lumen 12 has a D-shaped cross section with a planer surface facing the sub lumen 13, while the sub lumen 13 is a flattened circular (or, rounded-rectangular) cross sectional area with a flattened surface facing the main lumen 12, as shown in FIG. 2.

Such a flexible tube has a diameter of, for example, about 2-3 mm and a length of, for example, about 2-4 m. According to the illustrative embodiment, the flexible tube is formed of lubricant plastic material such as polytetrafluoroethylene (PTFE) resin or polyethylene resin.

As shown in FIG. 1, at the distal end portion of the flexible tube 10, side holes 14 are formed. Through the side holes 14, the inside of the balloon 11 and the sub lumen 13 communicate with each other. At the tip end of the balloon 11, an end mouthpiece 15 is secured. At the tip end of the sub lumen 13, a stopper cap 16 is inserted.

An element 20 is a connector arranged at the proximal end of the flexible tube 12. The connector 20 is configured such that a tool insertion mouthpiece 22 through which a treatment tool and the like is inserted and fed toward the main lumen 12 protrudes rearward (i.e., in the proximal end direction) straightly from a main body portion 21, and that an air injection mouthpiece 23 through which air is supplied to the sub lumen 13, protrudes obliquely rearward from the main body portion 21.

FIG. 3 is a perspective view of a part of the connector 20. As shown in FIG. 3, a main lumen connecting pipe 24 and a sub lumen connecting pipe 25 protrude straightly frontward from the main body portion 21. The main lumen connecting pipe 24 is detachably inserted into a proximal end portion of the main lumen 12 and straightly extends to communicate the tool insertion mouthpiece 22. The sub lumen connecting pipe 25 is detachably inserted into a proximal end portion of the sub lumen 13 and communicates with the injection mouthpiece 23.

FIG. 4 shows a cross sectional view of the main lumen connecting pipe 24 and the sub lumen connecting pipe 25 taken along line IV-IV of FIG. 1. The main lumen connecting pipe 24 and the sub lumen connecting pipe 25 have cross sectional shapes corresponding to the inner cross sectional shapes of the main lumen 12 and the sub lumen 13, respectively, so that the main lumen connecting pipe 24 and the sub lumen connecting pipe 25 are respectively fitted in the main lumen 12 and the sub lumen 13 without clearance therebetween.

According to the first embodiment, the sub lumen connecting pipe 25 is formed to have a length within a range of about 2-3 cm, and the main lumen connecting pipe 24 is formed to have a length which is about twice as long as that of the sub lumen connecting pipe 25 (see FIGS. 1 and 3).

A tip end portion 24a which is a portion longer than the sub lumen connecting pipe 25 is tapered such that a tip side portion has a smaller external size. Similarly, a tip end portion 25a of the sub lumen connecting pipe 25 is tapered such that a tip side portion has a smaller external size.

The indwelling balloon catheter configured as described above is used such that the flexible tube 10 is inserted through the treatment tool channel of the endoscope, and the tip end thereof is guided to an objective area, for example, bile duct. The balloon 11 is inflated, and only the endoscope is pulled out, with leaving the flexible tube 10.

After the endoscope is pulled out, the connector 20 is connected at the proximal end of the flexible tube 10. When the connector 20 is coupled, if necessary, a user may cut off the proximal end portion of the flexible tube 10 by several centimeters. If unnecessary, the user connects the connector 20 directly to the proximal end of the flexible tube 10.

Figure 5:
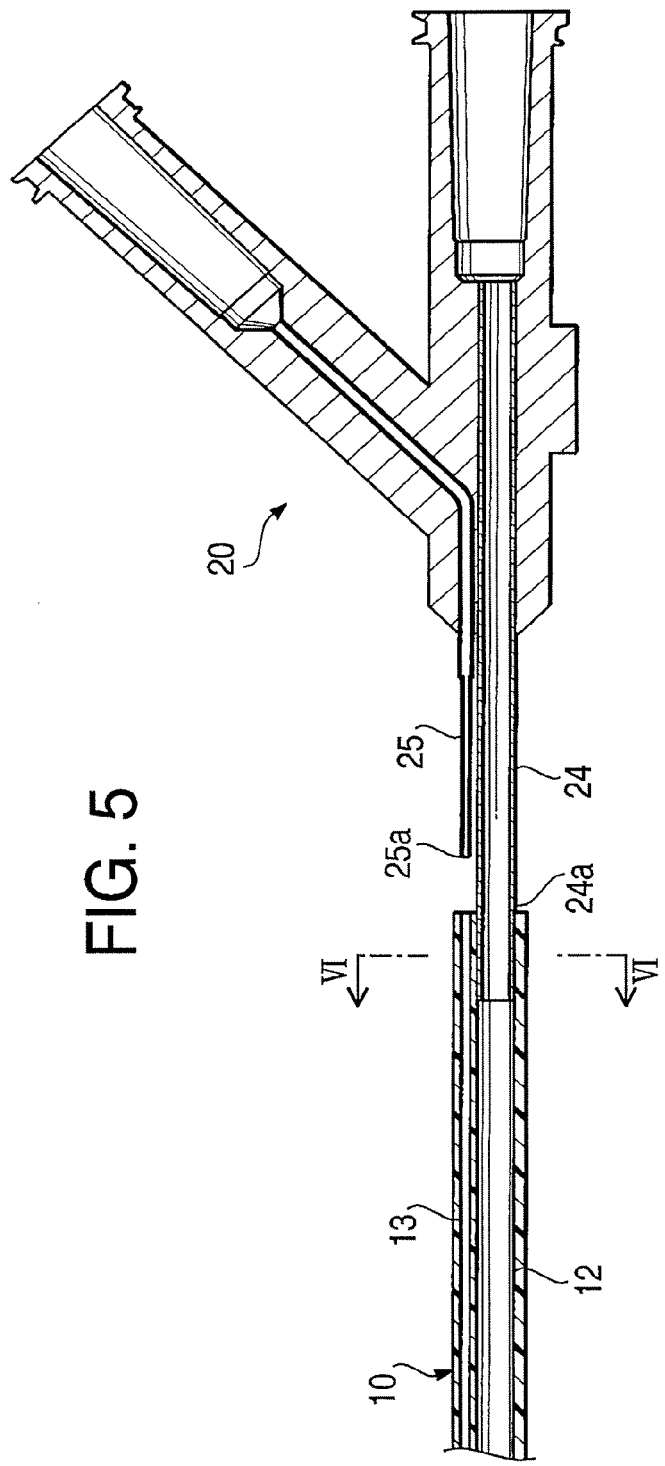
FIG. 5 is a cross-sectional side view showing a condition where a connector is being connected to a flexible tube of the indwelling balloon catheter to the connector according to aspects of the first embodiment of the invention.

In either case, as shown in FIG. 5, the user inserts the main lumen connecting pipe 24, which protrudes forward with respect to the sub lumen connecting pipe 25, into the main lumen 12. Since the portion 24a is tapered, the user can insert the main lumen connecting pipe 24 in the main lumen 12 relatively easily.

Figure 6:
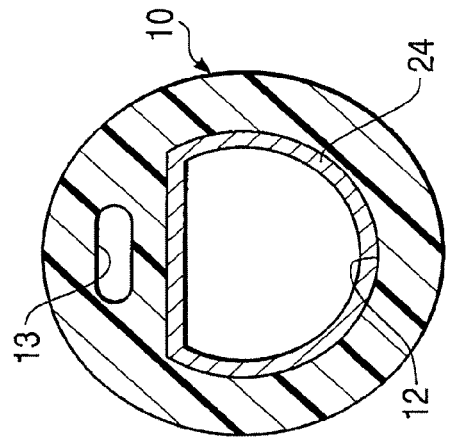
FIG. 6 is a cross-sectional view of the indwelling balloon catheter taken along line VI-VI of FIG. 5 according to aspects of the first embodiment of the invention.

As shown in FIG. 6, which is a cross sectional view taken along line VI-VI of FIG. 5, the main lumen connecting pipe 24 cannot rotate with respect to the main lumen 12 due to its D-shaped cross section. As a user keeps inserting the main lumen connecting pipe 24 in the main lumen 12, the tip end portion 25a of the sub lumen connecting pipe 25 is introduced to the opening of the sub lumen 13. Since the tip end portion 25a is tapered, as shown in FIG. 7, the sub lumen connecting pipe 25 can be inserted in the sub lumen 13 relatively smoothly.

As described above, even in a relatively dark environment, once the main lumen connecting pipe 24 is inserted in the proximal end of the main lumen 12, the sub lumen connecting pipe 25 can be inserted in the proximal end of the sub lumen 13 easily.

Figure 7:
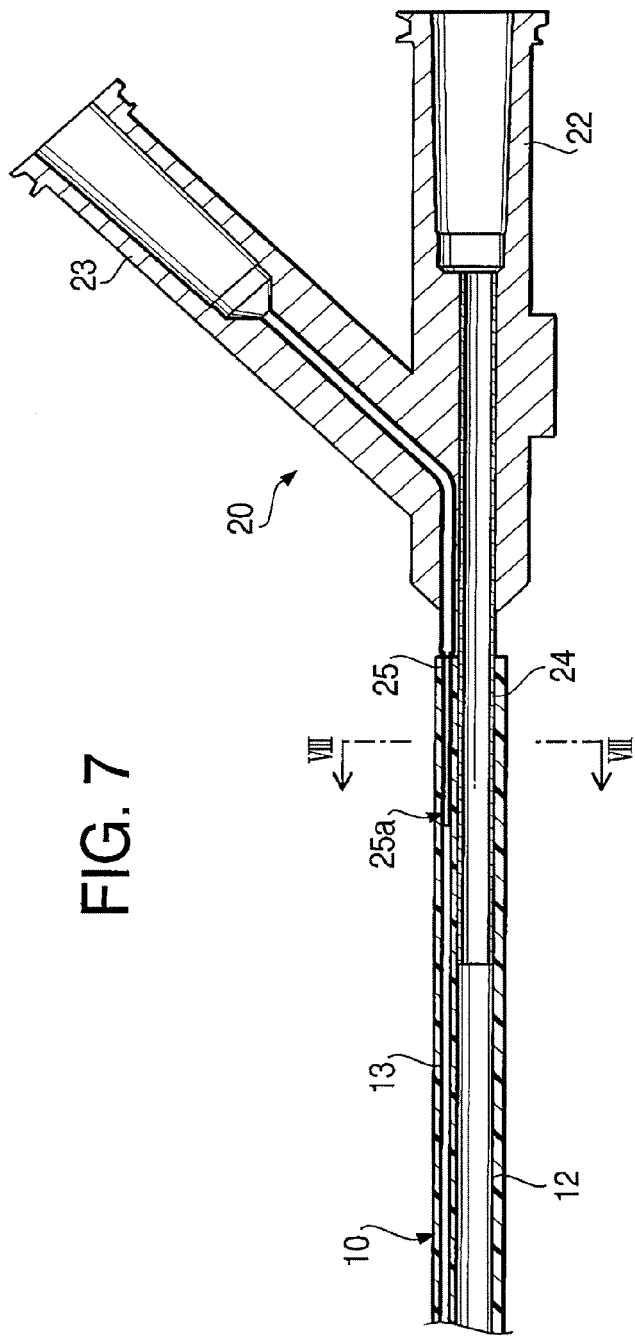
FIG. 7 is a cross-sectional side view showing a condition where the connector is connected to the flexible tube of the indwelling balloon catheter for the endoscope connected to the connector, in accordance with a first embodiment of the present invention.
Figure 8:
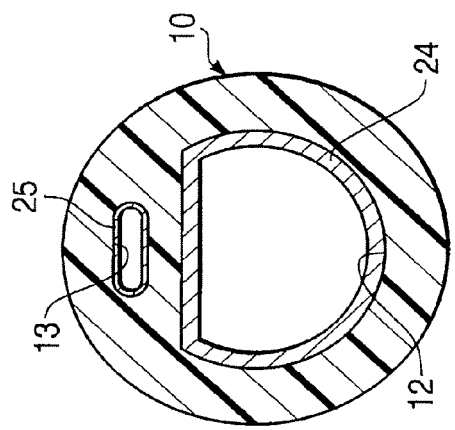
FIG. 8 is a cross-sectional view of an indwelling balloon catheter taken along line VIII-VIII of FIG. 7 according to aspects of the first embodiment of the invention.

As a result, as shown in FIG. 8 which is a cross section taken along line VIII-VIII of FIG. 7, the main lumen connecting pipe 24 is deeply inserted into the main lumen 12, and the sub lumen connecting pipe 25 is tightly inserted into the sub lumen 13. In this state, by connecting an injection syringe or the like to the injection mouthpiece 23 and feeding the air into the sub lumen 13, the balloon 11 can be inflated appropriately, and thus, it is ensured that the balloon catheter can be secured inside the human cavity, and kept in place.

According to the above-described configuration, if the sub lumen connecting pipe 25 is bent in a direction approaching to the main lumen connecting pipe 24, due to an external force, it becomes difficult or almost impossible to insert the sub lumen connecting pipe 25 into the sub lumen 13.

Figure 9:
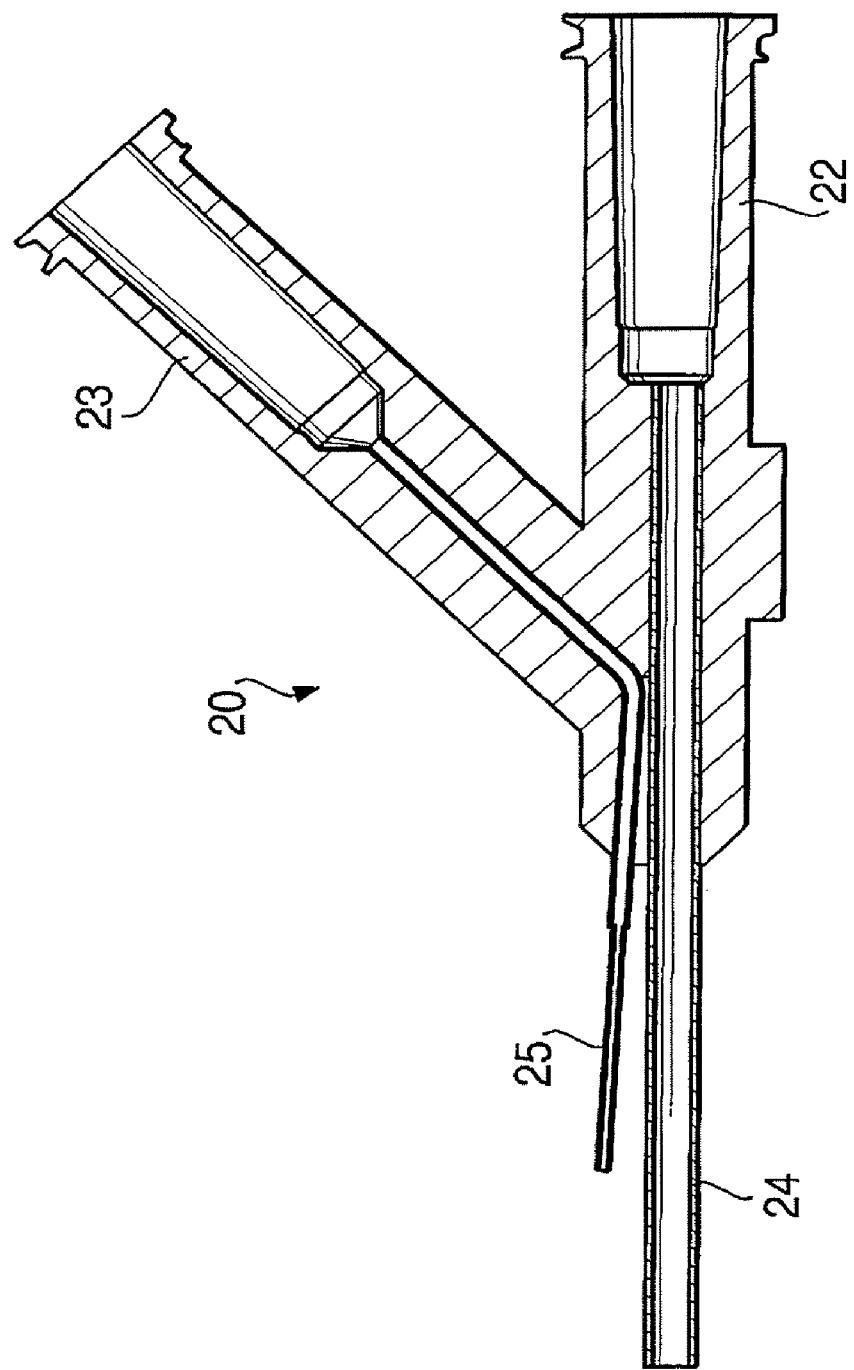
FIG. 9 is a cross-sectional side view of a connector of an indwelling balloon catheter according to aspects of a second embodiment of the invention.

FIG. 9 is a cross-sectional side view of a connector of an indwelling balloon catheter according to aspects of a second embodiment, which handles the above problem. According to the second embodiment, a portion of the sub lumen connecting pipe 25 protruding from the connector 20 extends obliquely. That is, the sub lumen connecting pipe 25 is configured such that a potion closer to the tip end of the sub lumen connecting pipe 25 is spaced farther from the main lumen connecting pipe 24. By elastically deforming the sub lumen connecting pipe 25 in the direction where it approaches the main lumen connecting pipe 24, the sub lumen connecting pipe 25 extends parallelly with the main lumen connecting pipe 24. The other configurations of the second embodiment are similar to those of the first embodiment.

Figure 10:
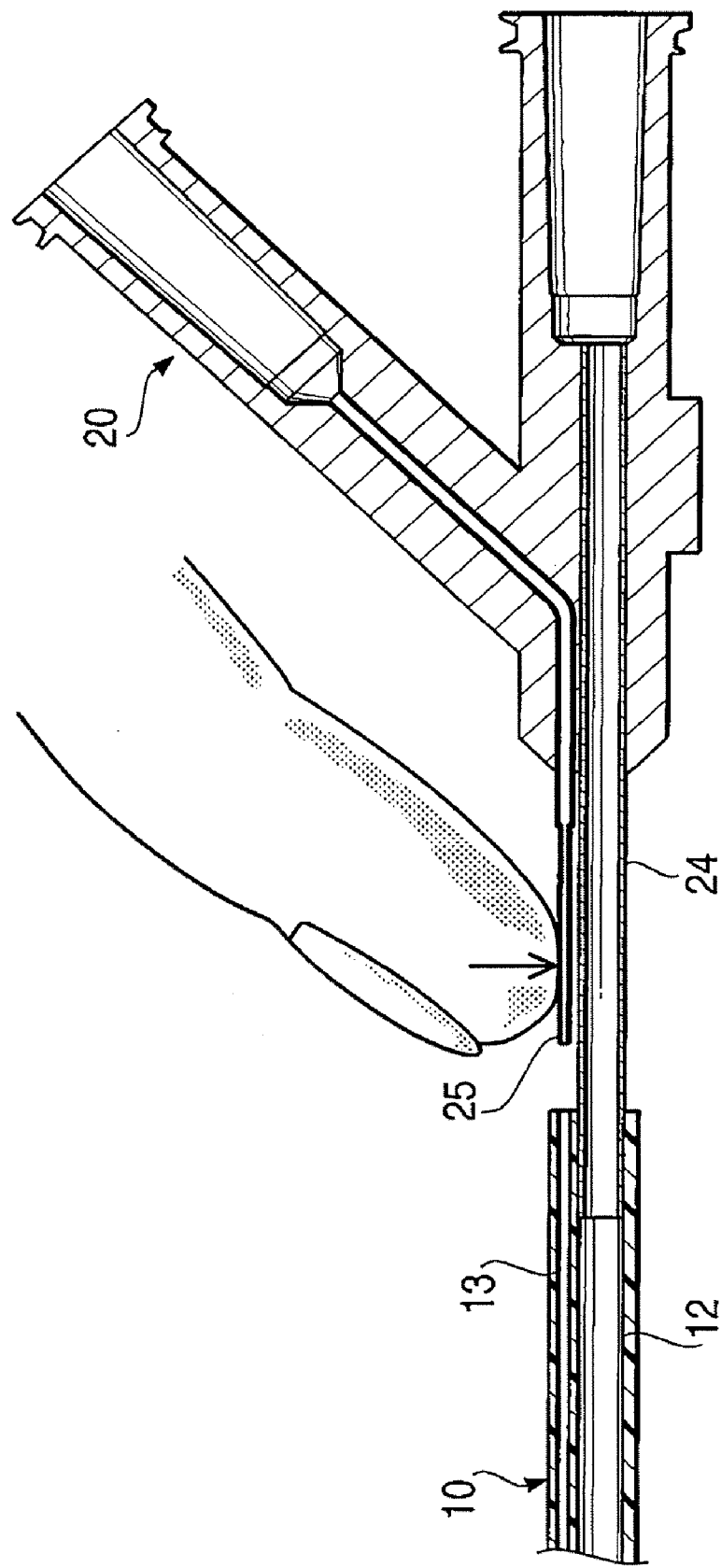
FIG. 10 is a cross-sectional side view showing a condition where a connector is being connected to a flexible tube of the indwelling balloon catheter to the connector according to aspects of the second embodiment of the invention.

With this configuration, as shown in FIG. 10, after inserting the main lumen connecting pipe 24 into the main lumen 12, the user can deform the sub lumen connecting pipe 25 by pushing the same toward the main lumen connecting pipe 24, and insert the sub lumen connecting pipe 25 into the sub lumen 13 relatively easily.

Figure 11:
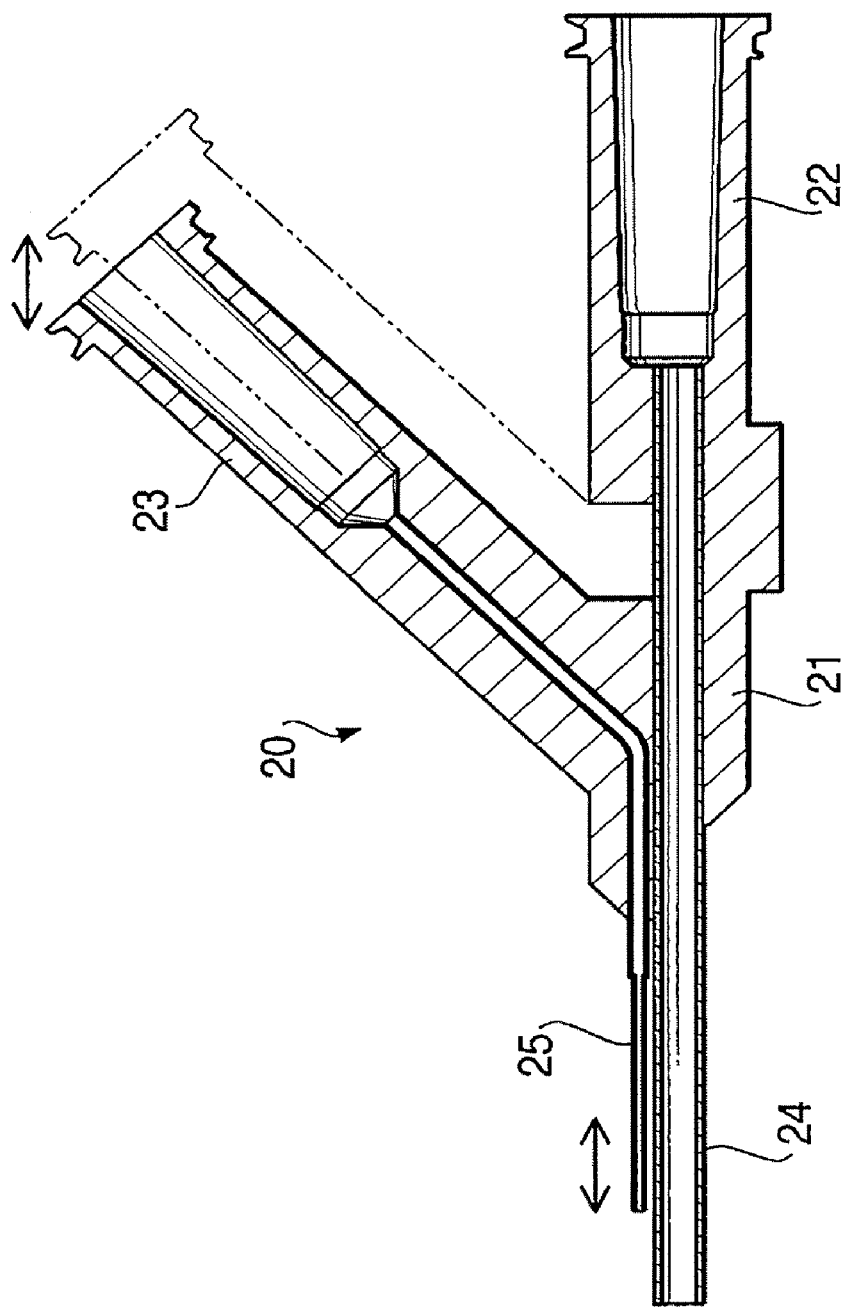
FIG. 11 is a cross-sectional side view of a connector of an indwelling balloon catheter according to aspects of a third embodiment of the invention.

FIG. 11 shows a connector 20 according to aspects of a third embodiment. The connector 20 according to the third embodiment is configured such that the sub lumen connecting pipe 25 and the injection mouthpiece 23 are slidable, with respect to the main lumen connecting pipe 24, in the axial direction of the main lumen connecting pipe 24. With this configuration, the manipulation of inserting the sub lumen connecting pipe 25 into the sub lumen 13 can be performed easily.

It is noted that the present invention has been described using non-limiting detailed descriptions of embodiments thereof that are provided by way of example and are not intended to limit the scope of the invention. For example, the shapes of the main lumen 12 and the main lumen connecting pipe 24 are not necessarily D-shaped, but any non-circular shapes can be used.

The present disclosure relates to the subject matter contained in Japanese Patent Application No. 2005-209414, filed on Jul. 20, 2005, which is expressly incorporated herein by reference in its entirety.

What is claimed is:

1. An indwelling balloon catheter for an endoscope, comprising:
a flexible tube including a first lumen and a second lumen, the first lumen and the second lumen being arranged in parallel with each other and extending in an axial direction of the flexible tube over an entire length thereof; and
a connector separate from the flexible tube and provided with a first connecting pipe and a second connecting pipe which protrude from a body of the connector, protruded portions of the first connecting pipe and the second connecting pipe being configured to be removably inserted into the first lumen and the second lumen, respectively,
wherein the protruded portion of the second connecting pipe is arranged obliquely with respect to the first connecting pipe such that a tip end of the protruded portion of the second connecting pipe is spaced farther from the first connecting pipe than an unprotruded portion of the second connecting pipe, the protruded portion of the second connecting pipe being configured to be elastically deformed to be parallel with the first connecting pipe,
wherein a cross sectional shape of the first lumen is a non-circular shape, a cross sectional shape of the first connecting pipe corresponds to the cross sectional shape of the first lumen,
wherein the cross sectional shapes of the first lumen and the first connecting pipe are larger than cross sectional shapes of the second lumen and the second connecting pipe, respectively, and
wherein the first connecting pipe protrudes longer from the connector than the second connecting pipe such that the first connecting pipe is used as a guide to insert the second connecting pipe into the second lumen.

2. The indwelling balloon catheter according to claim 1, wherein the flexible tube is a double lumen flexible tube which is configured such that the first lumen and the second lumen are formed integrally over the entire length of the flexible tube.

3. The indwelling balloon catheter according to claim 1, wherein the cross sectional shape of the second lumen has a flat portion on the first lumen side, and wherein the cross sectional shape of the second connecting pipe has a flat portions corresponding to the flat portion of the second lumen.

4. The indwelling balloon catheter according to claim 1, wherein the second connecting pipe is tapered so that a portion closer to a tip end is smaller in size.

5. The indwelling balloon catheter according to claim 1, a cross sectional shape of the first lumen is D-shaped with a flattened surface facing the second lumen, a cross sectional shape of the first connecting pipe corresponds to the cross sectional shape of the first lumen.

6. The indwelling balloon catheter according to claim 1, wherein a portion of the first connecting pipe protruding farther from a tip end of the second lumen is configured to be tapered to have a smaller size at a portion closer to a tip end of the first connecting pipe.

7. The indwelling balloon catheter according to claim 1, wherein the second connecting pipe being slidable with respect to the first connecting pipe in an axial direction of the first connecting pipe.

8. The indwelling balloon catheter according to claim 1, wherein the first lumen is a passage lumen allowing a predetermined substance to pass through, and wherein the second lumen is a ventilation lumen for feeding air therethrough.

9. The indwelling balloon catheter according to claim 8, wherein the predetermined substance includes a small radiation source.

10. The indwelling balloon catheter according to claim 3, wherein each of the second lumen and the second connecting pipe has a rounded-rectangular cross section.

11. The indwelling balloon catheter according to claim 1, wherein the first connecting pipe and the second connecting pipe do not contact one another over their entire lengths after the second connecting pipe is elastically deformed.

12. The indwelling balloon catheter according to claim 1, wherein the second connecting pipe is arranged obliquely with respect to the first connecting pipe as the first connecting pipe and the second connecting pipe each protrude from the body of the connector.

13. The indwelling balloon catheter according to claim 1, wherein the protruded portion of the second connecting pipe comprises a base section extending from the connector, and a distal section that protrudes from the base section to the tip end of the second connecting pipe, and
wherein the distal section is thinner than the base section in a radial direction such that the distal section can be inserted into the second lumen, and a lower portion of the base section is closer to the first connecting pipe than a lower portion of the distal section such that the protruded portion of the second connecting pipe can be elastically deformed to be parallel with the first connecting pipe.

* * * * *